US006869946B2

(12) United States Patent
Jacobsen et al.

(10) Patent No.: US 6,869,946 B2
(45) Date of Patent: Mar. 22, 2005

(54) SUBSTITUTED AZABICYCLIC MOIETIES FOR THE TREATMENT OF DISEASE

(75) Inventors: Eric Jon Jacobsen, Richland, MI (US); Daniel Patrick Walker, Kalamazoo, MI (US); Jason K. Myers, Kalamazoo, MI (US); David W. Piotrowski, Portage, MI (US); Vincent E. Groppi, Jr., Kalamazoo, MI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/124,145

(22) Filed: Apr. 17, 2002

(65) Prior Publication Data

US 2003/0055043 A1 Mar. 20, 2003

Related U.S. Application Data

(60) Provisional application No. 60/284,950, filed on Apr. 19, 2001, and provisional application No. 60/348,904, filed on Oct. 26, 2001.

(51) Int. Cl.⁷ .................. C07D 453/02; C07D 487/08; A61K 31/44

(52) U.S. Cl. ...................... 514/216; 514/299; 514/305; 514/413; 540/482; 546/112; 546/133; 548/452

(58) Field of Search .......................... 540/482; 546/112, 546/113; 548/452; 514/216, 299, 305, 413

(56) References Cited

U.S. PATENT DOCUMENTS

| | | | |
|---|---|---|---|
| 3,702,324 A | 11/1972 | Skinner et al. | 260/293.53 |
| 4,093,734 A | 6/1978 | Kruger et al. | 424/274 |
| 4,593,034 A | 6/1986 | Munson et al. | 514/305 |
| 4,605,652 A | 8/1986 | Welstead, Jr. | 514/214 |
| 4,657,911 A | 4/1987 | Imbert et al. | 514/272 |
| 4,717,563 A | 1/1988 | Alphin et al. | 424/10 |
| 4,721,720 A | 1/1988 | Wootton et al. | 514/304 |
| 4,797,387 A | 1/1989 | King | 514/212 |
| 4,798,829 A | 1/1989 | King et al. | 514/214 |

(List continued on next page.)

FOREIGN PATENT DOCUMENTS

| | | | |
|---|---|---|---|
| DE | 3810552 A1 | 10/1989 | C07D/451/12 |
| EP | 327335 A1 | 2/1988 | A61K/31/405 |
| EP | 353371 A1 | 2/1990 | A61K/31/505 |
| FR | 2625678 | 1/1988 | A61K/31/435 |
| WO | WO 91/09593 | 7/1991 | A61K/31/00 |
| WO | WO 92/11259 | 7/1992 | C07D/451/04 |
| WO | WO 92/15579 | 9/1992 | C07D/451/00 |
| WO | WO96/40100 | 12/1996 | A61K/31/165 |
| WO | WO97/30998 | 8/1997 | C07D/453/02 |
| WO | WO 98/47481 | 10/1998 | A61K/9/00 |
| WO | WO 00/73431 A2 | 12/2000 | C12N/15/00 |
| WO | WO 01/29034 | 4/2001 | C07D/453/02 |
| WO | WO 01/36417 A1 | 5/2001 | C07D/451/04 |
| WO | WO 01/60821 | 8/2001 | C07D/453/02 |
| WO | WO 01/85727 | 11/2001 | C07D/453/06 |

OTHER PUBLICATIONS

Levin, E.D., Nicotinic acetylcholine involvement in cognitive function in animals, Psychopharmacology, 138:217–230, 1998.*

Layzer, Degenerative Diseases of the Nervous System, Cecil Textbook of Medicine, 20th Edition, vol. 2, pp. 2050–7, 1996.*

Damasio, Alzheimer's Disease and Related Dementias, Cecil Textbook of Medicine, 20th Edition, vol. 2, pp. 1992–6, 1996.*

Bannon, A.W., *American Association for the Advancement of Science*. Broad–Spectrum, Non–Opiodid Analgesic Activity by Selective Modulation of Neuronal Nicotinic Acetylcholine Receptors. vol. 279, No. 5347, pp. 77–81, 1998.

Dineley, K.T., and James W. Patrick, *The Journal of Biological Chemistry*. Amino Acid Determinants of •7 Nicotinic Acetylcholine Receptor Surface Expression. vol. 275, No. 18, pp. 13974–13985, May 5, 2000.

Eisele, Jean–Luc. *Letters to Nature*. Chimaeric nicotinic–serotonergic receptor combines distinct ligand binding and channel specificities. vol. 366, pp. 479–483, Dec. 2, 1993.

(List continued on next page.)

*Primary Examiner*—Deepak Rao
(74) *Attorney, Agent, or Firm*—Peter C. Richardson; Lorraine B. Ling; Andrea E. Dorigo

(57) ABSTRACT

The invention provides compounds of Formula I:

Formula I

[Chemical structure: Cl-phenyl-C(=O)-NH-CH(R₁)-CH-N bicyclic system with R₂, m¹, m²]

wherein m¹ is 0 or 1;
m² is 1 or 2;
R₁ is —H, alkyl, halogenated alkyl, substituted alkyl, cycloalkyl, or phenyl;
R₂ is —H, alkyl, halogenated alkyl, substituted alkyl, cycloalkyl, or phenyl, provided that when m¹ is 1 at least one of R₁ and R₂ is —H; or a pharmaceutically acceptable salt, pharmaceutical composition, a pure enantiomer or racemic mixture thereof. The invention also provides a method for treating a disease or condition in a mammal, wherein the α7 nicotinic acetylcholine receptor is implicated and for treating diseases where there is a sensory-gating deficit in a mammal comprising administering to a mammal a therapeutically effective amount of a compound of Formula I. These compounds may be in the form of pharmaceutical salts or compositions, and may be in pure enantiomeric form or may be racemic mixtures.

14 Claims, No Drawings

U.S. PATENT DOCUMENTS

| | | |
|---|---|---|
| 4,820,715 A | 4/1989 | Monkovic et al. ............ 514/214 |
| 4,835,162 A | 5/1989 | Abood ........................ 514/305 |
| 4,863,919 A | 9/1989 | Smith ......................... 514/214 |
| 4,870,181 A | 9/1989 | Lo ............................. 546/133 |
| 4,877,780 A | 10/1989 | Vega-Noverola et al. ... 514/161 |
| 4,908,370 A | 3/1990 | Naylor et al. ............... 514/305 |
| 4,910,193 A | 3/1990 | Buchheit .................... 514/216 |
| 4,920,227 A | 4/1990 | Pelletier et al. ............. 546/133 |
| 4,983,600 A | 1/1991 | Ward et al. ................. 514/214 |
| 5,017,580 A | 5/1991 | Naylor et al. ............... 514/299 |
| 5,025,022 A | 6/1991 | Naylor et al. ............... 514/305 |
| 5,039,680 A | 8/1991 | Impoerato et al. .......... 514/304 |
| 5,057,519 A | 10/1991 | Suberg ....................... 514/282 |
| 5,070,095 A | 12/1991 | Jagdmann et al. .......... 514/305 |
| 5,084,460 A | 1/1992 | Munson, Jr. et al. ....... 514/282 |
| 5,175,173 A | 12/1992 | Sun ............................. 514/305 |
| 5,206,246 A | 4/1993 | Langlois et al. ............ 514/272 |
| 5,236,931 A | 8/1993 | Jagdmann et al. .......... 514/305 |
| 5,237,066 A | 8/1993 | Dorme et al. ............... 546/133 |
| 5,273,972 A | 12/1993 | Jagdmann et al. .......... 514/210 |
| 5,290,938 A | 3/1994 | Johansen .................... 546/133 |
| 5,561,149 A | 10/1996 | Azria et al. ................. 514/397 |
| 5,723,103 A | 3/1998 | De Paulis et al. .......... 424/1.85 |
| 5,741,819 A | 4/1998 | Illig et al. ................... 514/297 |
| 5,837,489 A | 11/1998 | Elliott et al. ............... 435/69.1 |
| 5,919,793 A | 7/1999 | Brown et al. ............... 514/305 |
| 5,977,144 A | 11/1999 | Meyer et al. ............... 514/334 |

OTHER PUBLICATIONS

Holladay, Mark W., et al., *Journal of Medicinal Chemistry.* Neuronal Nicotine Acetylcholine Receptors as Targets for Drug Discovery. Dec. 19, 1997.

Kem, William R. *Behavioral Brain Research.* "The brain α7 nicotinic receptor may be an important therapeutic target for the treatment of Alzheimer's disease: studies with DMXBA (GTS–21)." 113 (2000) 169–181.

Kuntzweiler, Theresa A., et al., *Drug Development Research.* "Rapid Assessment of Ligand Actions with Nicotinic Acetylcholine Receptors Using Calcium Dynamics and FLIPR." vol. 44, No. 1, pp. 14–20, May 1998.

Macor, JE. *Biorganic & Medicinal Chemistry Letters.* "The 5–HT$_3$ Antagonist Tropisetron (ICS 205–930) is a Potent and Selective α7 Nicotinic Receptor Partial Agonist." 11 (2001) 319–321.

* cited by examiner

SUBSTITUTED AZABICYCLIC MOIETIES FOR THE TREATMENT OF DISEASE

CROSS REFERENCE TO RELATED APPLICATIONS

This application claims the benefit of U.S. provisional application Serial No. 60/284,950 filed on Apr. 19, 2001, under 35 USC 119(e)(i) and U.S. provisional application Serial No. 60/348,904 filed on Oct. 26, 2001, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides a method for treating a disease or condition in a mammal where the α7 nicotinic acetylcholine receptor is implicated and for treating diseases where there is a sensory-gating deficit in a mammal.

BACKGROUND OF THE INVENTION

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, Nature, 366(6454), p. 360–4, 1997). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., Nature, 366(6454), p 479–83, 1993), and the pore forming C-terminal domain of the 5-HT$_3$ receptor expressed well in Xenopus oocytes while retaining nicotinic agonist sensitivity. Eisele et al. used the N-terminus of the avian (chick) form of the α7 nAChR receptor and the C-terminus of the mouse form of the 5-HT$_3$ gene. However, under physiological conditions the α7 nAChR is a calcium channel while the 5-HT$_3$R is a sodium and potassium channel. Indeed, Eisele et al. teaches that the chicken α7 nAChR/mouse 5-HT$_3$R behaves quite differently than the native α7 nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

SUMMARY OF THE INVENTION

The present invention discloses compounds of Formula I:

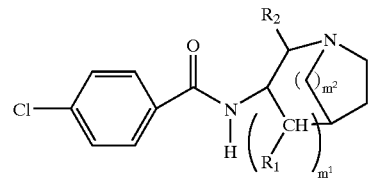

Formula I wherein $m^1$ is 0 or 1;
$m^2$ is 1 or 2;
$R_1$ is —H, alkyl, halogenated alkyl, substituted alkyl, cycloalkyl, or phenyl;
$R_2$ is —H, alkyl, halogenated alkyl, substituted alkyl, cycloalkyl, or phenyl;
or a pharmaceutically acceptable salt, pharmaceutical composition, pure enantiomer, or racemic mixture thereof.

The compounds of Formula I are useful for treating a disease or condition in a mammal, wherein the α7 nicotinic acetylcholine receptor is implicated and for treating diseases where there is a sensory-gating deficit in a mammal comprising administering to a mammal a therapeutically effective amount of said compound or a pharmaceutically acceptable salt, pharmaceutical composition, pure enantiomer, or racemic mixture thereof.

DETAILED DESCRIPTION OF THE INVENTION

Surprisingly, we have found that compounds of Formula I:

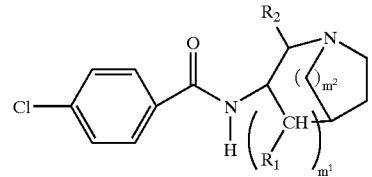

Formula I wherein $m^1$ is 0 or 1;
$m^2$ is 1 or 2;
$R_1$ is —H, alkyl, halogenated alkyl, substituted alkyl, cycloalkyl, or phenyl;
$R_2$ is —H, alkyl, halogenated alkyl, substituted alkyl, cycloalkyl, or phenyl;
Alkyl is both straight- and branched-chain moieties having from 1–6 carbon atoms;
Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Substituted alkyl is an alkyl moiety from 1–6 carbon atoms and having 0–3 substituents independently selected from —F, —Cl, —Br, or —I and further having 1 substituent selected from —OR$_5$, —SR$_5$, —NR$_5$R$_5$, —C(O)R$_5$, —C(O)NR$_5$R$_5$, —CN, —NR$_5$C(O)R$_5$, —S(O)$_2$NR$_5$R$_5$, —NR$_5$S(O)$_2$R$_5$, —NO$_2$, phenyl, or phenyl having 1 substituent selected from R$_{11}$ and further having 0–3 substituents independently selected from —F, —Cl, —Br, or —I;

Cycloalkyl is a cyclic alkyl moiety having from 3–6 carbon atoms;

Each R$_5$ is independently —H, alkyl, cycloalkyl, heterocycloalkyl, alkyl substituted with 1 substituent selected from R$_6$, cycloalkyl substituted with 1 substituent selected from R$_6$, heterocycloalkyl substituted with 1 substituent selected from R$_6$, halogenated alkyl, halogenated cycloalkyl, halogenated heterocycloalkyl, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —OR$_5$, —SR$_5$, —NR$_5$R$_5$, —C(O)R$_5$, —CN, —C(O)NR$_5$R$_5$, —NR$_5$C(O)R$_5$, —S(O)$_2$NR$_5$R$_5$, —NR$_5$S(O)$_2$R$_5$, —NO$_2$, phenyl, or phenyl having 1 substituent selected from R$_8$ and further having 0–3 substituents independently selected from —F, —Cl, —Br, or —I;

Heterocycloalkyl is a cyclic moiety having 4–7 atoms with 1–2 atoms within the ring being —S—, —N(R$_9$)—, or —O—;

Halogenated heterocycloalkyl is a cyclic moiety having from 4–7 atoms with 1–2 atoms within the ring being —S—, —N(R$_9$)—, or —O—, and having 1–4 substituents independently selected from —F, or —Cl;

Substituted heterocycloalkyl is a cyclic moiety having from 4–7 atoms with 1–2 atoms within the ring being —S—, —N(R$_9$)—, or —O— and having 0–3 substituents independently selected from —F, or —Cl, and further having 1 substituent selected from —OR$_5$, —SR$_5$, —NR$_5$R$_5$, —C(O)R$_5$, —C(O)NR$_5$R$_5$, —CN, —NR$_5$C(O)R$_5$, —NO$_2$, —S(O)$_2$NR$_5$R$_5$, —NR$_5$S(O)$_2$R$_5$, phenyl, or phenyl having 1 substituent selected from R$_8$ and further having 0–3 substituents independently selected from —F, —Cl, —Br, or —I;

Substituted phenyl is a phenyl either having 1–4 substituents independently selected from —F, —Cl, —Br, or —I, or having 1 substituent selected from R$_{10}$ and 0–3 substituents independently selected from —F, —Cl, —Br, or —I;

R$_6$ is —OR$_7$, —SR$_7$, —NR$_7$R$_7$, —C(O)R$_7$, —C(O)NR$_7$R$_7$, —CN, —CF$_3$—S(O)$_2$NR$_7$R$_7$, —NR$_7$S(O)$_2$R$_7$, or —NO$_2$;

Each R$_7$ is independently —H, alkyl, cycloalkyl, heterocycloalkyl, halogenated alkyl, halogenated cycloalkyl, or halogenated heterocycloalkyl;

R$_8$ is alkyl, cycloalkyl, heterocycloalkyl, halogenated alkyl, halogenated cycloalkyl, halogenated heterocycloalkyl, —OR$_7$, —SR$_7$, —NR$_7$R$_7$, —C(O)R$_7$, —C(O)NR$_7$R$_7$, —CN, —NR$_7$C(O)R$_7$, —S(O)$_2$NR$_7$R$_7$, —NR$_7$S(O)$_2$R$_7$, —NO$_2$, alkyl substituted with 1-4 substituent(s) independently selected from —F, —Cl, —Br, —I, or R$_6$, cycloalkyl substituted with 1–4 substituent(s) independently selected from —F, —Cl, —Br, —I, or R$_6$, or heterocycloalkyl substituted with 1–4 substituent(s) independently selected from —F, —Cl, —Br, —I, or R6;

R$_9$ is —H, alkyl, halogenated alkyl, substituted alkyl, cycloalkyl, halogenated cycloalkyl, substituted cycloalkyl, phenyl, —SO$_2$R$_{11}$, or phenyl having 1 substituent selected from R$_{11}$ and further having 0–3 substituents independently selected from —F, —Cl, —Br, or —I;

R$_{10}$ is —OR$_7$, —SR$_7$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —NR$_7$R$_7$, —C(O)R$_7$, —NO$_2$, —C(O)NR$_7$R$_7$, —CN, —NR$_7$C(O)R$_7$, —S(O)$_2$NR$_7$R$_7$, or —NR$_7$S(O)$_2$R$_7$; and Each R$_{11}$ is independently —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, or substituted phenyl; or a pharmaceutically acceptable salt, pharmaceutical composition, pure enantiomer, or racemic mixture thereof are useful for treating a disease or condition in a mammal, wherein the α7 nicotinic acetylcholine receptor is implicated and for treating diseases where there is a sensory-gating deficit in a mammal comprising administering to a mammal a therapeutically effective amount of said compound.

A group of compounds of Formula I includes compounds wherein R$_1$ is H. Another group of compounds of Formula I includes compounds wherein R$_1$ is alkyl, halogenated alkyl, substituted alkyl, cycloalkyl, or phenyl. Another group of compounds of Formula I includes compounds wherein R$_2$ is H. Another group of compounds of Formula I includes compounds wherein R$_2$ is alkyl, halogenated alkyl, substituted alkyl, cycloalkyl, or phenyl.

Another group of compounds of Formula I includes compounds wherein m$^1$ is 0 and m$^2$ is 2 giving a quinuclidine ring:

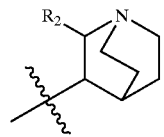

When m$^1$ is 0, there is no R$_1$.

Another group of compounds of Formula I includes compounds wherein m$^1$ is 0 and m$^2$ is 2 and the C3 carbon of the quinuclidine has the R configuration:

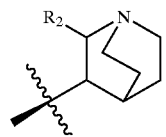

Another group of compounds of Formula I includes compounds wherein $m^1$ is 0 and $m^2$ is 1 giving

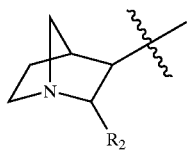

Another group of compounds of Formula I includes compounds wherein $m^1$ is 1 and $m^2$ is 1 giving

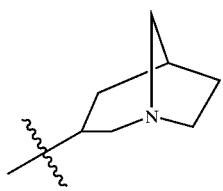

Another group of compounds of Formula I includes compounds wherein $m^1$ is 1 and $m^2$ is 1 giving

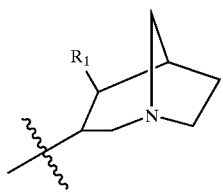

Another group of compounds of Formula I includes compounds wherein $m^1$ is 1 and $m^2$ is 1 giving

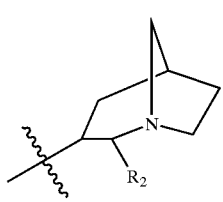

Another group of compounds of Formula I includes compounds wherein $m^1$ is 1 and $m^2$ is 1 giving

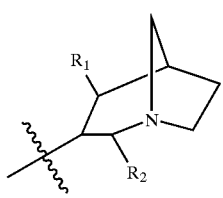

Another group of compounds of Formula I includes compounds wherein $m^1$ is 1 and $m^2$ is 2 giving

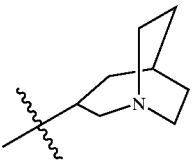

Another group of compounds of Formula I includes compounds wherein $m^1$ is 1 and $m^2$ is 2 giving

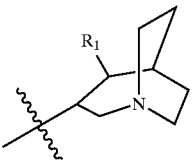

Another group of compounds of Formula I includes compounds wherein $m^1$ is 1 and $m^2$ is 2 giving

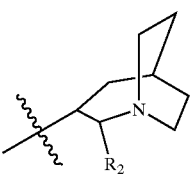

Another group of compounds of Formula I includes compounds wherein $m^1$ is 1 and $m^2$ is 2 giving

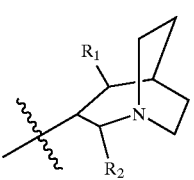

The compounds of the present invention having the quinuclidine ring ($m^1$ is 0 and $m^2$ is 2) have an optically active center. The invention involves using a compound being substantially the 3R isomer and substantially free of the 3S isomer on the quinuclidine ring. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

The compounds of Formula I have optically active center(s) on the [2.2.1] azabicyclic ring ($m^1$ is 0 and $m^2$ is 1) at C3 and C4 when $R_2$ is H. The scope of this invention includes the separate stereoisomers of Formula I being endo-4S, endo-4R, exo-4S, exo-4R:

endo-4S
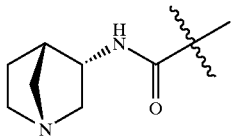

endo-4R
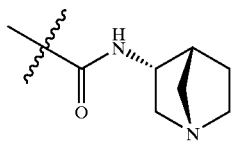

exo-4S
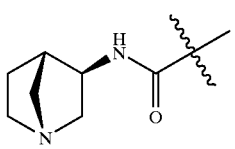

exo-4R
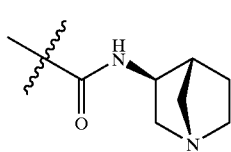

The endo isomer is the isomer where the non-hydrogen substituent at C3 of the [2.2.1] azabicyclic compound is projected toward the larger of the two remaining bridges. The exo isomer is the isomer where the non-hydrogen substituent at C3 of the [2.2.1] azabicyclic compound is projected toward the smaller of the two remaining bridges. Thus, there can be four separate isomers: exo-4(R), exo-4(S), endo-4(R), and endo-4(S).

The compounds of Formula I have optically active center(s) on the [3.2.1] azabicyclic ring at C3 and C5 ($m^1$ is 1 and $m^2$ is 1) when $R_2$ is H. The scope of this invention includes the separate stereoisomers of Formula I being endo-3S, 5R, endo-3R, 5S, exo-3R, 5R, exo-3S, 5S:

endo-3S, 5R
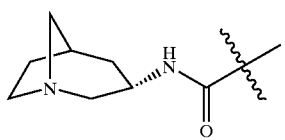

endo-3R, 5S
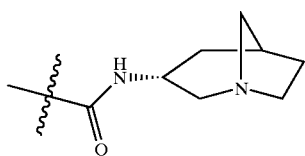

exo-3R, 5R
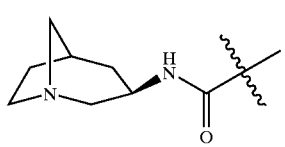

exo-3S, 5S
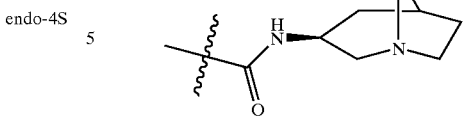

The compounds of Formula I have optically active centers on the [3.2.2] azabicyclic ring with one center being at C3 when $R_2$ is H. The scope of this invention includes the separate stereoisomers of Formula I being 3(S) and 3(R):

3(S)
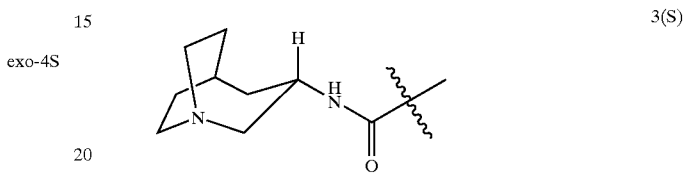

3(R)
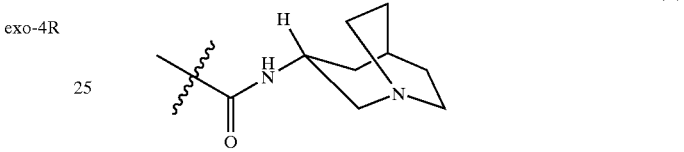

The compounds of the present invention having the specified stereochemistry above have different levels of activity and that for a given set of values for the variable substitutuents one isomer may be preferred over the other isomers. Although it is desirable that the stereochemical purity be as high as possible, absolute purity is not required. This invention involves racemic mixtures and compositions of varying degrees of stereochemical purities when $R_2$ is H and when $R_2$ is other than H. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

Abbreviations which are well known to one of ordinary skill in the art may be used (e.g., "Ph" for phenyl, "Me" for methyl, "Et" for ethyl, "h" or "hr" for hour or hours, "min" for minute or minutes, and "rt" or "RT" for room temperature).

All temperatures are in degrees Centigrade.

Room temperature is within the range of 15–25 degrees Celsius.

AChR refers to acetylcholine receptor.

nAChR refers to nicotinic acetylcholine receptor.

$5HT_3R$ refers to the serotonin-type 3 receptor.

α-btx refers to α-bungarotoxin.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TMS refers to tetramethylsilane.

MLA refers to methyllycaconitine.

Ether refers to diethyl ether.

HPLC refers to high pressure liquid chromatography.

MeOH refers to methanol.

EtOH refers to ethanol.

IPA refers to isopropyl alcohol.

THF refers to tetrahydrofuran.

DMSO refers to dimethylsulfoxide.
DMF refers to dimethylformamide.
EtOAc refers to ethyl acetate.
TMS refers to tetramethylsilane.
TEA refers to triethylamine.
DIEA refers to N,N-diisopropylethylamine.
HATU refers to O-(7-azabenzotriazol-1-yl)-N,N,N',N'-tetramethyluronium hexafluorophosphate.
DPPA refers to diphenylphosphoryl azide.
Halogen is F, Cl, Br, or I.

The carbon atom content of various hydrocarbon-containing moieties is indicated by a prefix designating the minimum and maximum number of carbon atoms in the moiety, i.e., the prefix $C_{i\text{-}j}$ indicates a moiety of the integer "i" to the integer "j" carbon atoms, inclusive. Thus, for example, $C_{1\text{-}6}$ alkyl refers to alkyl of one to six carbon atoms.

Mammal denotes human and other mammals.

The compound of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1\text{-}6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The amount of therapeutically effective compound that is administered and the dosage regimen for treating a disease condition with the compound and/or composition of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001 to 100 mg/kg/day for an adult, preferably in the range of about 0.1 to 50 mg/kg/day for an adult. A total daily dose of about 1 to 1000 mg of active ingredient may be appropriate for an adult. The daily dose can be administered in one to four doses per day.

In addition to the compound of the present invention, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence with α7 nAChR but functionally the two ligand-gated ion channels are very different. For example, α7 nAChR is rapidly inactivated, is highly permeable to calcium and is activated by acetylcholine and nicotine. On the other hand, 5HT$_3$R is inactivated slowly, is relatively impermeable to calcium and is activated by serotonin. These experiments suggest that the α7 nAChR and 5HT$_3$R proteins have some degree of homology, but function very differently. Indeed the pharmacology of the channels is very different. For example, Ondansetron, a highly selective 5HT$_3$R antagonist, has little activity at the α7 nAChR. The converse is also true. For example, GTS-21, a highly selective α7 nAChR agonist, has little activity at the 5HT$_3$R.

α7 nAChR is a ligand-gated Ca$^{++}$ channel formed by a homopentamer of α7 subunits. Previous studies have established that α-bungarotoxin (α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E .D., *Psychopharmacology*, 108:417–31, 1992; Levin, E. D. and Simon B. B., *Psychopharmacology*, 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., *Psychopharmacology (Berl).*, 142(4):334–42, March 1999; Wilens, T. E. et. al., *Am. J. Psychiatry*, 156(12):1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "atypical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencephlographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.*, 10:131–41, 1993). These data reflect a schizophrenic's inability to "filter" or ignore unimportant information. The sensory gating deficit appears to be one of the key pathological features of this disease (Cadenhead, K. S. et. al., *Am. J. Psychiatry*, 157:55–9, 2000). Multiple studies show that nicotine normalizes the sensory deficit of schizophrenia (Adler, L. E. et. al., *Am. J. Psychiatry*, 150:1856–61, 1993). Pharmacological studies indicate that nicotine's effect on sensory gating is via the α7 nAChR (Adler, L. E. et. al., *Schizophr. Bull.*, 24:189–202, 1998). Indeed, the biochemical data indicate that schizophrenics have 50% fewer of α7 nAChR receptors in the hippocampus, thus giving a rationale to partial loss of α7 nAChR functionality (Freedman, R. et. al., *Biol. Psychiatry*, 38:22–33, 1995). Interestingly, genetic data indicate that a polymorphism in the promoter region of the α7 nAChR gene is strongly associated with the sensory gating deficit in schizophrenia (Freedman, R. et. al., *Proc. Nat'l Acad. Sci. USA*, 94(2):587–92, 1997; Myles-Worsley, M. et. al., *Am. J. Med. Genet*, 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and 5HT$_3$R. To conduct such an assay, one uses cell lines that expressed functional forms of the α7 nAChR using the α7/5-HT$_3$ channel as the drug target and cell lines that expressed functional 5HT$_3$R. In both cases, the ligand-gated ion channel were expressed in SH-EP1 cells. Both ion channels can produce robust signal in the according FLIPR assay.

The compound of the present invention is an α7 nAChR agonists and may be used to treat a wide variety of diseases. For example, it may be used for treating a disease or condition in a mammal, wherein the α7 nicotinic acetylcholine receptor is implicated and for treating diseases where there is a sensory-gating deficit in a mammal comprising administering to a mammal a therapeutically effective amount of said compound or a pharmaceutically acceptable salts thereof.

Finally, the compound of the present invention may be used in combination therapy with typical and atypical antipsychotic drugs. Such combination therapy lowers the effective dose of the anti-psychotic drug and thereby reduces the side effects of the anti-psychotic drug. Some typical antipsychotic drugs that may be used in the practice of the invention include Haldol. Some atypical anti-psychotic drugs include Ziprasidone, Olanzapine, Resperidone, and Quetiapine.

Compounds of Formula I can be prepared as shown in Scheme 1. The key step in the preparation of this class of compounds is the coupling of an azabicyclic moiety with the requisite acid chloride (Lv=Cl), mixed anhydride (e.g., Lv=diphenyl phosphoryl, bis(2-oxo-3-oxazolidinyl) phosphinyl, or acyloxy of the general formula of O—C(O)—R$_{Lv}$, where R$_{Lv}$ includes phenyl or t-butyl), or carboxylic acid (Lv=OH) in the presence of an activating reagent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as HATU).

Scheme 1

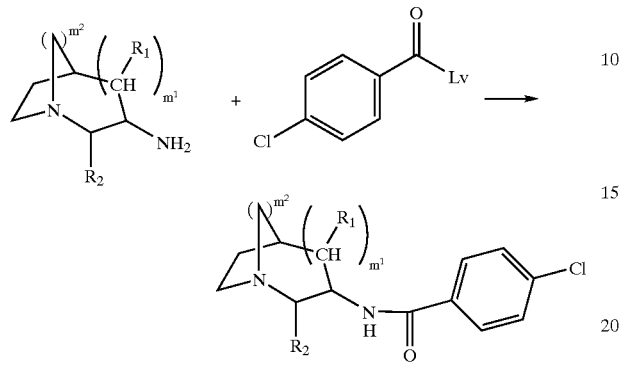

Generally, the acid is activated using HATU or is converted to the acyl azide by using DPPA. The appropriate amine (where $m^1$ is 0 and $m^2$ is 1 or 2, or $m^1$ is 1 and $m^2$ is 2) is reacted with TEA and added to a solution of the appropriate anhydride or azide to give the desired final compounds.

However, for $m^1$ is 1 and $m^2$ is 1, the acid is converted into a mixed anhydride by treatment with bis (2-oxo-3-oxazolidinyl) phosphinic chloride in the presence of TEA with $CH_2Cl_2$ or $CHCl_3$ as the solvent. The resulting anhydride solution is directly reacted with 1-azabicyclo[3.2.1]octan-3-amine added neat or using DMF or aqueous DMF as solvent. In some cases, the ester (Lv being OMe or OEt) may be reacted directly with the amine in refluxing methanol or ethanol to give the compounds of Formula I.

One of ordinary skill in the art will recognize that the methods described for the reaction of the unsubstituted 3-aminoquinuclidine ($R_2$=H) are equally applicable to substituted compounds ($R_2 \neq H$). Such compounds can be prepared by reduction of the oxime of the corresponding 3-quinuclidinone (see *J. Labelled Compds. Radiopharm.*, 53–60 (1995) and *J. Med. Chem.* 988–995, (1998)). The oximes can be prepared by treatment of the 3-quinuclidinones with hydroxylamine hydrochloride in the presence of a base. The 3-quinuclidinones, where $R_2$=substituted alkyl, cycloalkyl, substituted benzyl, can be prepared by known procedures (see *Tet. Lett.* 1015–1018, (1972), *J. Am. Chem. Soc.* 1278–1291 (1994), *J. Am. Chem. Soc.* 4548–4552 (1989), *Tetrahedron*, 1139–1146 (2000)). The 3-quinuclidinones, where $R_2$=aryl, can be prepared by palladium catalyzed arylation as described in *J. Am. Chem. Soc.* 1473–1478 (1999) and *J. Am. Chem. Soc.* 1360–1370 (2000).

One of ordinary skill in the art will also recognize that the methods described for the reaction of the unsubstituted 3-amino-1-azabicyclo[2.2.1]heptane ($R_2$=H) are equally applicable to substituted compounds ($R_2 \neq H$). Such compounds can be prepared as described in *Tetrahedron*, (1997), 53, p 11121.

One of ordinary skill in the art will also recognize that the methods described for the reaction of the unsubstituted 1-azabicyclo[3.2.1]octan-3-amine or 1-azabicyclo[3.2.2]nonan-3-amine ($R_2$=H) are equally applicable to substituted compounds ($R_2 \neq H$). The $R_2$ substituent may be introduced as known to one skilled in the art through standard alkylation chemistry. Exposure of 1-azabicyclo[3.2.1]octan-3-one or 1-azabicyclo[3.2.2]nonan-3-one to a hindered base such as LDA (lithium diisopropylamide) in a solvent such as THF or ether between 0° C. to −78° C. followed by the addition of an alkylating agent ($R_2Lv$, where Lv=Cl, Br, I, OTs, etc.) will, after being allowed to warm to about 0° C. to rt followed by an aqueous workup, provide the desired compound as a mixture of isomers. Chromatographic resolution (flash, HPLC, or chiral HPLC) will provided the desired purified alkylated ketones. From there, formation of the oxime and subsequent reduction will provide the desired endo or exo isomers.

EXAMPLE 1(a)

Quinuclidine Ring ($m^1$ is 0 and $m^2$ is 2)

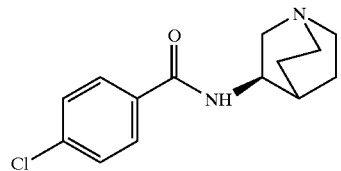

It is well known in the literature how to prepare the compound of the present invention for the quinuclidine ring, for example, see U.S. Pat. No. 5,017,580 or U.S. Pat. No. 5,206,246.

EXAMPLE 1(b)

4-chloro-N-[2-methyl-1-azabicyclo[2.2.2]oct-3-yl] benzamide 4-methylbenzenesulfonate

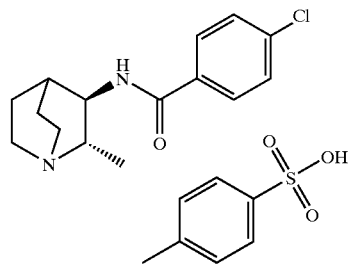

Example 1(b)(i) - 2S, 3R

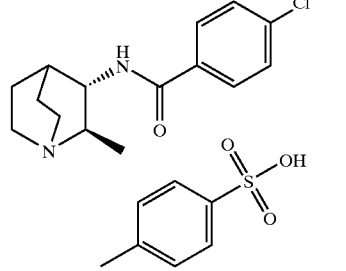

Example 1(b)(ii) - 2R, 3S

Preparation of 2-methylquinuclidin-3-one.

A mixture of 2-methylene-3-quinuclidinone dihydrate hydrochloride (27.18 g, 0.1296 mol, 1 eq) and $K_2CO_3$ (86.0 g, 0.6213 mol, 4.8 eq) is dissolved in 130 mL water and 250 mL $CH_2Cl_2$ and stirred vigorously. After 3 days, the layers are separated and the aqueous layer is extracted with $CH_2Cl_2$. The combined organic layers are dried ($MgSO_4$), filtered and concentrated to give 17.8 g (100%) of 2-methylenequinuclidin-3-one as a yellow oil. MS (ESI) for $C_8H_{11}NO$ m/z 138.1 ($M^+$).

Preparation of 2-methylquinuclidin-3-one.

2-Methylenequinuclidin-3-one (17.8 g, 0.1296 mol, 1 eq) is dissolved in 40 mL methanol in a Parr hydrogenation bottle. A THF slurry of 10% Pd/C (0.57 g) is added. The mixture is hydrogenated for 45 min at 45 psi, recharging as needed. The mixture is filtered through a pad of Celite. The Celite is washed with excess methanol. The solution is concentrated to give a solid and a yellow oil. The mixture is taken up in ether, filtered and concentrated to provide 16.2 g (90%) of 2-methylquinuclidin-3-one. MS (ESI) for $C_8H_{13}NO$ m/z 140.2 ($M^+$).

Preparation of (3E/Z)-2-methyl-1-azabicyclo[2.2.2]octan-3-one oxime hydrochloride.

2-Methylquinuclidin-3-one (39.59 g, 0.2844 mol, 1 eq) and hydroxylamine hydrochloride (20.0 g, 0.2878 mol, 1.01 eq) are dissolved in 170 mL absolute EtOH. The mixture is heated under reflux until a clear solution develops (about 20 min), after which is immediately followed by formation of a white precipitate. The reaction is cooled and allowed to stand overnight. The mixture is cooled in an ice bath, the solids are filtered and dried (house vacuum) to provide 46.4 g of (3E/Z)-2-methyl-1-azabicyclo[2.2.2]octan-3-one oxime hydrochloride. A second crop of 2.4 g is also obtained. Overall yield 48.8 g (90%). The 2-methyl-1-azabicyclo[2.2.2]octan-3-one oxime hydrochloride is a 4:1 mixture of oxime isomers. MS (ESI) for $C_8H_{14}N_2O$ m/z 154.8 ($M^+$). Partial $^1$H NMR (400 MHz, DMSO) δ 4.39 (0.2H), 4.29 (0.8H), 1.57 (0.64H), 1.47 (2.4H).

Preparation of trans 2-methyl-1-azabicyclo[2.2.2]octan-3-amine dihydrochloride.

A solution of sodium n-propoxide (prepared from 5.5 g sodium (0.24 mol) and 100 mL n-propanol) is added dropwise to a suspension of 2-methyl-1-azabicyclo[2.2.2]octan-3-one oxime hydrochloride (45.8 g, 0.24 mol, 1 eq) in 150 mL n-propanol. After complete addition, 250 mL of n-propanol is added and the mixture is heated under reflux. Sodium (55.2 g, 2.40 mol, 10 eq.) is added in portions to the refluxing mixture. The mixture is heated under reflux overnight. After about 14 h, the mixture is cooled, water is added and the layers are separated. The n-propanol layer is washed with brine and dried ($MgSO_4$). The combined aqueous layers are extracted with $CHCl_3$ and dried ($MgSO_4$). The combined, dried organic layers are treated with about 70 mL concentrated HCl. The solvent is removed in vacuo. Absolute EtOH is added and the solvent is removed. The sequence is repeated 2–3 times with fresh EtOH until a white solid forms. Absolute EtOH is added, the solids are filtered and dried (vacuum oven, about 60° C.) to provide 36.5 g of trans 3-amino-2-methylquinuclidine dihydrochloride. MS (ESI) for $C_8H_{16}N_2$ m/z 141.3 ($M^+$). Additional material is obtained from the mother liquor: 7.8 g ($2^{nd}$ crop) and 1.5 g ($3^{rd}$ crop), both as a trans/cis mixture of isomers.

Preparation of 4-chloro-N-[(2S,3R)-2-methyl-1-azabicyclo[2.2.2]oct-3-yl]benzamide:

4-Chlorobenzoic acid (26.3 g, 0.1681 mol, 1.1 eq) and TEA (106 mL, 0.764 mol, 5 eq.) are dissolved in 300 mL THF. Diphenylphosphoryl chloride (32.0 mL, 0.1681 mol, 1.1 eq) is added dropwise. After 1 h, trans 2-methylquinuclidin-3-amine dihydrochloride (32.6 g, 0.1528 mol, 1 eq) is added. The mixture is allowed to stir at RT overnight. 1N NaOH (about 100 mL) is added and the pH is adjusted to pH 11 with 50% NaOH and about 50 g $K_2CO_3$. The layers are separated. The aqueous layer is extracted with $CHCl_3$. The combined organic layers are dried ($MgSO_4$), filtered and concentrated. The residue is taken up in heptane and concentrated to give 35.1 g (82%) of 4-chloro-N-(2-methyl-1-azabicyclo[2.2.2]oct-3-yl)phenyl-2-carboxamide as a light yellow solid. The enantiomers are separated on a 5×50 cm Chiralcel OD column at 30° C., eluting with 15% IPA/heptane+0.1% DEA (v/v/v) mobile phase, 90 mL/min flow rate and UV detection at 249 nm. Injections of 900 mg (in 18 mL of IPA) are made. Two collections are made with one being from 1–8 min and the second one being from 11–16 min. Reanalysis on a 0.46×25 cm Chiralcel OD-H column, 15% IPA/85% heptane/0.1% DEA mobile phase, 0.5 mL/min flow rate, UV detection at 250 nm is used. The compound having the 2S, 3R stereochemistry elutes at 9.9 min while the compound having the 2R, 3S stereochemistry elutes at 12.9 min.

Example 1(b)(i): The p-toluenesulfanate salt is prepared and recrystallized from EtOH/EtOAc to give 4-chloro-N-[(2S,3R)-2-methyl-1-azabicyclo[2.2.2]oct-3-yl]benzamide 4-methylbenzenesulfonate. $[\alpha]^{25}_D$=+3° (c 0.96, methanol); HRMS (FAB) calcd for $C_{15}H_{19}ClN_2O$ +H 279.1264, found 279.1272.

Example 1(b)(ii): The p-toluenesulfonate salt is prepared and recrystallized from acetone/heptane to give 4-chloro-N-[(2R,3S)-2-methyl-1-azabicyclo[2.2.2]oct-3-yl]benzamide 4-methylbenzenesulfonate. $[\alpha]^{25}_D$=−3° (c 0.89, methanol).

EXAMPLE 1(c)

Trans N-[2-Benzyl-1-Azabicyclo[2.2.2]Oct-3-Yl]-4-Chlorobenzamide Hydrochloride

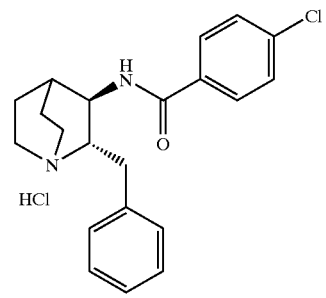

Preparation of 2-benzylquinuclidin-3-one.

A mixture of 3-quinuclidinone (6.25 g, 50 mmol), benzaldehyde (5.83 g, 55 mmol) and KOH (0.84 g, 15 mmol) in 30 mL MeOH is heated under reflux for 16 h. The reaction is cooled and water is added. The mixture is extracted with $CHCl_3$, dried ($MgSO_4$), filtered and concentrated. The yellow solid is triturated with warm heptane, filtered and dried to provide 6.6 g (62%) of 2-benzylidene-1-azabicyclo[2.2.2]octan-3-one. A suspension of 2-benzylidene-1-azabicyclo[2.2.2]octan-3-one (6.6 g, 31 mmol) in MeOH is treated with a THF slurry of 10% Pd/C (0.38 g) in a Parr hydrogenation bottle. The bottle is charged with 40 psi of hydrogen gas and allowed to shake for 1 h. The mixture is filtered through Celite, and the solvent is removed in vacuo. The residue is purified by chromatography (Biotage 40M, 30% EtOAc/hexanes—100% EtOAc) to afford 0.48 g (7%) of 2-benzylidene-1-azabicyclo[2.2.2]octan-3-ol and 4.8 g (72%) of 2-benzylquinuclidin-3-one. MS (ESI+) for $C_{14}H_{17}NO$ m/z 216.1 $(M+H)^+$.

Preparation of Cis 2-benzyl-1-azabicyclo[2.2.2]octan-3-ol.

A solution of 2-benzylquinuclidin-3-one (4.8 g, 22.4 mmol) in 20 mL THF is cooled to −78° C. and treated with L-selectride (30.0 mL, 1.0M in THF). After 1 h, additional L-selectride is added (10 mL, 1.0M in THF). After 1 h, additional THF (30 mL) and L-selectride (30 mL, 1.0M in THF) are added. The reaction is allowed to warm to RT over 2 h. The mixture is carefully quenched with 20 mL water and then conc. HCl until the pH of the aqueous layer is pH 1. The aqueous layer is washed with Et$_2$O (discarded), made basic (pH 11) with 50% NaOH and extracted with CHCl$_3$. The combined CHCl$_3$ layers are dried (MgSO$_4$), filtered and concentrated to give a solid. The solid is recrystallized from CH$_3$CN to provide 4.6 g (94%) of the product as white needles. HRMS (FAB) calcd for C$_{14}$H$_{19}$NO+H 218.1545, found 218.1541.

Preparation of trans 3-azido-2-benzylquinuclidine.

A solution of cis 2-benzyl-1-azabicyclo[2.2.2]octan-3-ol (4.2 g, 19 mmol) is dissolved in 20 mL pyridine. The mixture is cooled to 0° C., treated with methanesulfonyl chloride (1.6 mL, 21 mmol) and allowed to warm to RT. After 16 h, 1N NaOH is added and the mixture is extracted with CHCl$_3$, dried (MgSO$_4$), filtered and concentrated. Cyclohexane is added and removed in vacuo (three times) to provide 4.0 g (71%) of a brown oil. MS (ESI+) for C$_{15}$H$_{21}$NO$_3$S m/z 296.2 (M+H)$^+$. The oil is dissolved in 17 mL DMF, treated with sodium azide (2.45 g, 37.7 mmol) and heated at 100° C. After 36 h, the reaction is cooled, water is added and the mixture is extracted with CHCl$_3$. The combined organic layers are washed with water, dried (MgSO$_4$), filtered and concentrated to provide 2.47 g (75%) of the product as an oil. MS (ESI+) for C$_{14}$H$_{18}$N$_4$ m/z 243.1 (M+H)$^+$.

Preparation of trans 2-benzylquinuclidin-3-amine.

A solution of trans 3-azido-2-benzylquinuclidine (2.47 g, 10.2 mmol) in EtOH is treated with a THF slurry of 10% Pd/C (0.25 g) in a Parr hydrogenation bottle. The bottle is charged with 45 psi of hydrogen gas and allowed to shake for 16 h. The mixture is filtered through Celite. The Celite is washed with excess EtOH and the solvent is removed in vacuo. The residue is purified by chromatography (Biotage 40S, 90:9:1 CHCl$_3$/MeOH/NH$_4$OH) to afford 1.5 g (68%) of trans 2-benzylquinuclidin-3-amine as an oil. MS (ESI+) for C$_{14}$H$_{20}$N$_2$ m/z 217.1 (M+H)$^+$.

Preparation of trans N-[2-benzyl-1-azabicyclo[2.2.2]oct-3-yl]-4-chlorobenzamide hydrochloride.

4-Chlorobenzoic acid (0.205 g, 1.3 mmol) and Et$_3$N (0.20 mL, 1.43 mmol) is dissolved in 6 mL THF and treated with diphenylphosphinic chloride (0.25 mL, 1.31 mmol). After 0.5 h, a solution of trans 2-benzylquinuclidin-3-amine (0.280 g, 1.29 mmol) in 4 mL THF is added. The reaction is allowed to stir at RT for 16 h after which 1N NaOH is added. The mixture is extracted with CHCl$_3$, dried (MgSO$_4$), filtered and concentrated to provide 0.41 g (88%) of a white solid. The hydrochloride salt is formed and recrystallized from IPA/EtOAc. HRMS (FAB) calcd for C$_{21}$H$_{23}$ClN$_2$O+H 355.1577, found 355.1563.

Using methods described herein, other examples can be prepared including N-(2-ethyl-1-azabicyclo[2.2.2]oct-3-yl)-4-chlorobenzamide as racemic mixtures or as enantiomers having any of the stereochemistry described herein.

3-Amino-1-azabicyclo[2.2.1]heptane (m$^1$ is 0 and m$^2$ is 1):

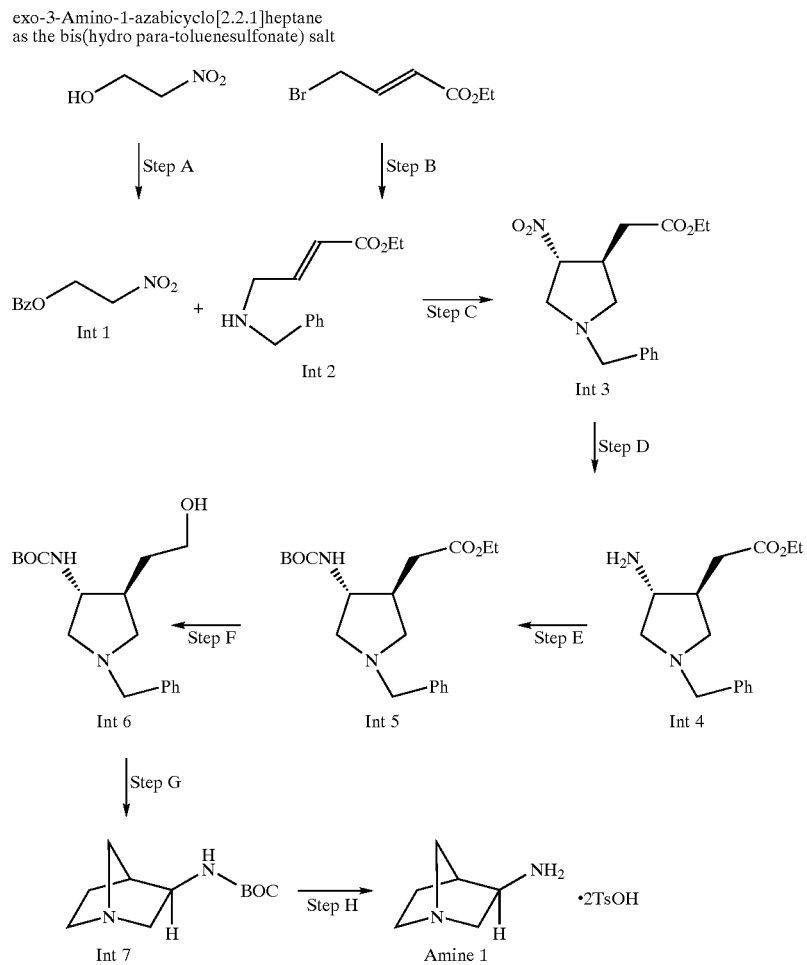

Step A. Preparation of 2-(benzoyloxy)-1-nitroethane (Int 1).

Benzoyl chloride (14.9 mL, 128 mmol) is added to a stirred solution of nitroethanol (9.2 mL, 128 mmol) in dry benzene (120 mL). The solution is refluxed for 24 hr and then concentrated in vacuo. The crude product is purified by flash chromatography on silica gel. Elution with hexanes-EtOAc (80:20) affords Int 1 as a white solid (68% yield): $^1$H NMR (CDCl$_3$) δ 8.0, 7.6, 7.4, 4.9, 4.8.

Step B. Preparation of ethyl E-4-(benzylamino)-2-butenoate (Int 2).

Ethyl E-4-bromo-2-butenoate (10 mL, 56 mmol, tech grade) is added to a stirred solution of benzylamine (16 mL, 146 mmol) in CH$_2$Cl$_2$ (200 mL) at rt. The reaction mixture stirs for 15 min, and is diluted with ether (1 L). The mixture is washed with saturated aqueous NaHCO$_3$ solution (3×) and water, dried over Na$_2$SO$_4$, filtered and concentrated in vacuo. The residue is purified by flash chromatography on silica gel. Elution with hexanes-EtOAc (70:30) affords Int 2 as a clear oil (62% yield): $^1$H NMR (CDCl$_3$) δ 7.4–7.2, 7.0, 6.0, 4.2, 3.8, 3.4, 2.1–1.8, 1.3.

Step C. Preparation of trans-4-nitro-1-(phenylmethyl)-3-pyrrolidineacetic acid ethyl ester (Int 3).

A solution of Int 1 (6.81 g, 34.9 mmol) and Int 2 (7.65 g, 34.9 mmol) in EtOH (70 mL) stirs at rt for 15 h and is then concentrated in vacuo. The residue is diluted with ether (100 mL) and saturated aqueous NaHCO$_3$ solution (100 mL). The organic layer is separated and dried over Na$_2$SO$_4$, filtered and concentrated in vacuo. The crude product is purified by flash chromatography on silica gel. Elution with hexanes-EtOAc (85:15) affords Int 3 as a clear oil (76% yield): $^1$H NMR (CDCl$_3$) δ 7.4–7.3, 4.8–4.7, 4.1, 3.8–3.6, 3.3–3.0, 2.7–2.6, 2.4–2.3, 1.2.

Step D. Preparation of trans-4-amino-1-(phenylmethyl)-3-pyrrolidineacetic acid ethyl ester (Int 4).

A mixture of Int 3 (3.28 g, 11.2 mmol) and RaNi (1.5 g) in EtOH (100 mL) is placed in a Parr bottle and hydrogenated for 4 h under an atmosphere of hydrogen (46 psi) at rt. The mixture is filtered through a pad of Celite, and the solvent is removed in vacuo to afford Int 4 as a clear oil (100% yield): $^1$H NMR (300 MHz, CDCl$_3$) δ 7.3–7.2, 4.1, 3.6, 3.2, 3.0–2.9, 2.8, 2.8–2.6, 2.6–2.4, 2.30–2.2, 1.2.

Step E. Preparation of trans-4-(1,1-dimethylethoxycarbonylamido)-1-(phenylmethyl)-3-pyrrolidineacetic acid ethyl ester (Int 5).

Di-tert-butyldicarbonate (3.67 g, 16.8 mmol) is added to a stirred solution of Int 4 (2.94 g, 11.2 mmol) in CH$_2$Cl$_2$ (30 mL) cooled in an ice bath. The reaction is allowed to warm to rt and stirred overnight. The mixture is concentrated in vacuo. The crude product is purified by flash chromatography on silica gel. Elution with hexanes-EtOAc (80:20) affords Int 5 as a white solid (77% yield): $^1$H NMR (300 MHz, CDCl$_3$) δ 7.4–7.2, 5.1–4.9, 4.1, 4.0–3.8, 3.6, 3.2–3.0, 2.8–2.6, 2.5–2.4, 2.3–2.1, 1.4, 1.3.

Step F. Preparation of trans-(tert-butoxycarbonylamino)-4-(2-hydroxyethyl)-1-(N-phenylmethyl) Pyrrolidine (Int 6).

LiAlH$_4$ powder (627 mg, 16.5 mmol) is added in small portions to a stirred solution of Int 5 (3.0 g, 8.3 mmol) in anhydrous THF (125 mL) in a −5° C. bath. The mixture is stirred for 20 min in a −5° C. bath, then quenched by the sequential addition of water (0.6 mL), 15% (w/v) aqueous NaOH (0.6 mL) and water (1.8 mL). Excess anhydrous K$_2$CO$_3$ is added, and the mixture is stirred for 1 h, then filtered. The filtrate is concentrated in vacuo. The residue is purified by flash chromatography on silica gel. Elution with EtOAc affords Int 6 as a white solid (94% yield): $^1$H NMR (CDCl$_3$) δ 7.4–7.3, 5.3–5.2, 4.1–4.0, 3.9–3.7, 3.3–3.2, 2.8–2.7, 2.3–2.1, 1.7, 1.5.

Int 6 is a racemic mixture that can be resolved via chromatography using a Diacel chiral pack AD column. From the two enantiomers thus obtained, the (+)-enantiomer, $[\alpha]^{25}_D$+35 (c 1.0, MeOH), gives rise to the corresponding optically pure exo-4-S final compounds, whereas the (−)-enantiomer, $[\alpha]^{25}_D$−34 (c 0.98, MeOH), gives rise to optically pure exo-4-R final compounds. The methods described herein use the (+)-enantiomer of Int 6 to obtain the optically pure exo-4-S final compounds. However, the methods used are equally applicable to the (−)-enantiomer of Int 6, making non-critical changes to the methods provided herein to obtain the optically pure exo-4-R final compounds.

Step G. Preparation of exo-3-(tert-butoxycarbonylamino)-1-azabicyclo[2.2.1]heptane (Int 7).

TEA (8.0 g, 78.9 mml) is added to a stirred solution of Int 6 (2.5 g, 7.8 mmol) in CH$_2$Cl$_2$ (50 mL), and the reaction is cooled in an ice-water bath. CH$_3$SO$_2$Cl (5.5 g, 47.8 mmol) is then added dropwise, and the mixture is stirred for 10 min in an ice-water bath. The resulting yellow mixture is diluted with saturated aqueous NaHCO$_3$ solution, extracted with CH$_2$Cl$_2$ several times until no product remains in the aqueous layer by TLC. The organic layers are combined, washed with brine, dried over Na$_2$SO$_4$ and concentrated in vacuo. The residue is dissolved in EtOH (85 mL) and is heated to reflux for 16 h. The reaction mixture is allowed to cool to rt, transferred to a Parr bottle and treated with 10% Pd/C catalyst (1.25 g). The bottle is placed under an atmosphere of hydrogen (53 psi) for 16 h. The mixture is filtered through Celite, and fresh catalyst (10% Pd/C, 1.25 g) is added. Hydrogenolysis continues overnight. The process is repeated three more times until the hydrogenolysis is complete. The final mixture is filtered through Celite and concentrated in vacuo. The residue is purified by flash chromatography on silica gel. Elution with CHCl$_3$—MeOH—NH$_4$OH (90:9.5:0.5) affords Int 7 as a white solid (46% yield): $^1$H NMR (CDCl$_3$) δ 5.6–5.5, 3.8–3.7, 3.3–3.2, 2.8–2.7, 2.0–1.8, 1.7–1.5, 1.5.

Step H. Preparation of exo-3-amino-1-azabicyclo[2.2.1]heptane bis(hydro-para-toluenesulfonate), amine 1.

Para-toluenesulfonic acid monohydrate (1.46 g, 7.68 mmol) is added to a stirred solution of Int 7 (770 mg, 3.63 mmol) in EtOH (50 mL). The reaction mixture is heated to reflux for 10 h, followed by cooling to rt. The precipitate is collected by vacuum filtration and washed with cold EtOH to give Amine 1 as a white solid (84% yield): $^1$H NMR (CD$_3$OD) δ 7.7, 7.3, 3.9–3.7, 3.7–3.3, 3.2, 2.4, 2.3–2.2, 1.9–1.8.

endo-3-Amino-1-azabicyclo[2.2.1]heptane as the bis(hydro para-toluenesulfonate) salt

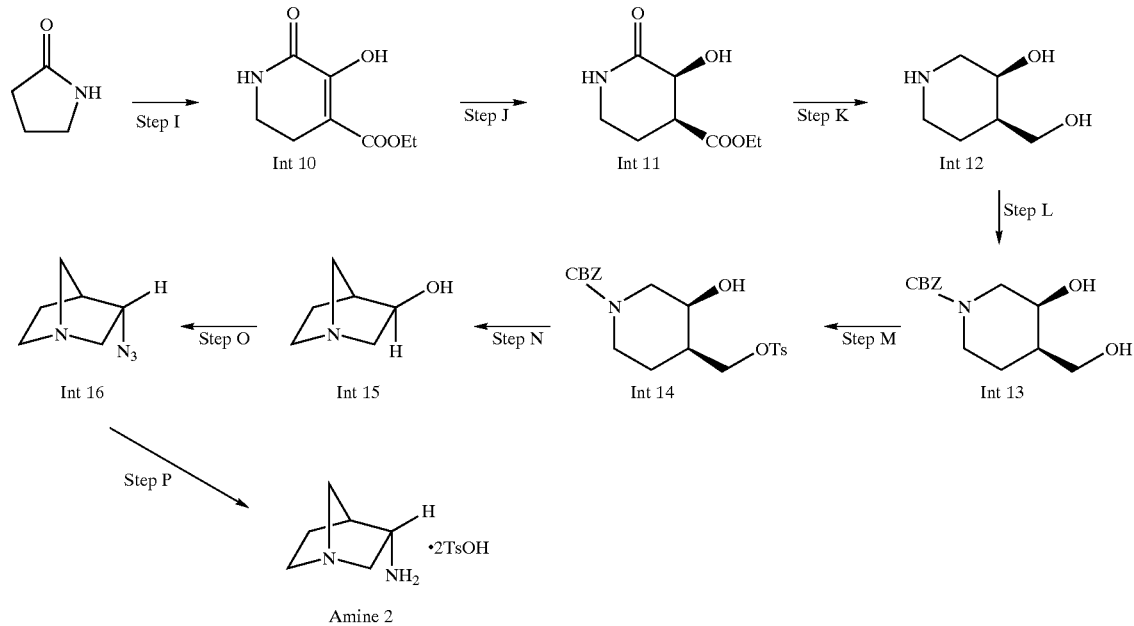

Amine 2

Step I. Preparation of ethyl 5-hydroxy-6-oxo-1,2,3,6-tetrahydropyridine-4-carboxylate (Int 10).

Absolute EtOH (92.0 mL, 1.58 mol) is added to a mechanically stirred suspension of potassium ethoxide (33.2 g, 395 mmol) in dry toluene (0.470 L). When the mixture is homogeneous, 2-pyrrolidinone (33.6 g, 395 mmol) is added, and then a solution of diethyl oxalate (53.1 mL, 390 mmol) in toluene (98 mL) is added via an addition funnel. After complete addition, toluene (118 mL) and EtOH (78 mL) are added sequentially. The mixture is heated to reflux for 18 h. The mixture is cooled to rt and aqueous HCl (150 mL of a 6.0 M solution) is added. The mixture is mechanically stirred for 15 min. The aqueous layer is extracted with $CH_2Cl_2$, and the combined organic layers are dried over $MgSO_4$, filtered and concentrated in vacuo to a yellow residue. The residue is recrystallized from EtOAc to afford Int 10 as a yellow solid (38% yield): $^1H$ NMR ($CDCl_3$) δ 11.4, 7.4, 4.3, 3.4, 2.6, 1.3.

Step J. Preparation of ethyl cis-3-hydroxy-2-oxopiperidine-4-carboxylate (Int 11).

A mixture of Int 10 (15 g, 81 mmol) and 5% rhodium on carbon (2.0 g) in glacial acetic acid is placed under an atmosphere of hydrogen (52 psi). The mixture is shaken for 72 h. The mixture is filtered through Celite, and the filtrate is concentrated in vacuo to afford Int 11 as a white solid (98% yield): $^1H$ NMR ($CDCl_3$) δ 6.3, 4.2, 4.0–3.8, 3.4, 3.3–3.2, 2.2, 1.3.

Step K. Preparation of cis-4-(hydroxymethyl)piperidin-3-ol (Int 12).

Int 11 (3.7 g, 19.9 mmol) as a solid is added in small portions to a stirred solution of $LiAlH_4$ in THF (80 mL of a 1.0 M solution) in an ice-water bath. The mixture is warmed to rt, and then the reaction is heated to reflux for 48 h. The mixture is cooled in an ice-water bath before water (3.0 mL, 170 mmol) is added dropwise, followed by the sequential addition of NaOH (3.0 mL of a 15% (w/v) solution) and water (9.0 mL, 500 mmol). Excess $K_2CO_3$ is added, and the mixture is stirred vigorously for 15 min. The mixture is filtered, and the filtrate is concentrated in vacuo to afford Int 12 as a yellow powder (70% yield): $^1H$ NMR (DMSO-$d_6$) δ 4.3, 4.1, 3.7, 3.5–3.2, 2.9–2.7, 2.5–2.3, 1.5, 1.3.

Step L. Preparation of benzyl cis-3-hydroxy-4-(hydroxymethyl)piperidine-1-carboxylate (Int 13).

N-(benzyloxy carbonyloxy)succinimide (3.04 g, 12.2 mmol) is added to a stirred solution of Int 12 (1.6 g, 12.2 mmol) in saturated aqueous $NaHCO_3$ (15 mL) at rt. The mixture is stirred at rt for 18 h. The organic and aqueous layers are separated. The aqueous layer is extracted with ether (3×). The combined organic layers are dried over anhydrous $K_2CO_3$, filtered and concentrated in vacuo to afford Int 13 as a yellow oil (99% yield): $^1H$ NMR ($CDCl_3$) δ 7.4–7.3, 5.2, 4.3, 4.1, 3.8–3.7, 3.0–2.8, 2.1, 1.9-1.7, 1.4.

Step M. Preparation of benzyl cis-3-hydroxy-4-[(4-methylphenyl)sulfonyl oxymethyl]piperidine-1-carboxylate (Int 14).

Para-toluenesulfonyl chloride (1.0 g, 5.3 mmol) is added to a stirred solution of Int 13 (3.6 g, 5.3 mmol) in pyridine (10 mL) in a —15° C. bath. The mixture is stirred for 4 h, followed by addition of HCl (4.5 mL of a 6.0 M solution). $CH_2Cl_2$ (5 mL) is added. The organic and aqueous layers are separated. The aqueous layer is extracted with $CH_2Cl_2$. The combined organic layers are washed with brine, dried over $MgSO_4$, filtered and concentrated in vacuo to afford Int 14 as a colorless oil (78% yield): $^1H$ NMR ($CDCl_3$) δ 7.8, 7.4–7.2, 5.1, 4.3–4.2, 4.1, 3.9–3.8, 2.9–2.7, 2.4, 1.9, 1.6–1.3.

Step N. Preparation of exo-1-azabicyclo[2.2.1]heptan-3-ol (Int 15).

A mixture of Int 14 (3.6 g, 8.6 mmol) and 10% Pd/C catalyst (500 mg) in EtOH (50 mL) is placed under an atmosphere of hydrogen. The mixture is shaken for 16 h. The mixture is filtered through Celite. Solid $NaHCO_3$ (1.1 g, 13 mmol) is added to the filtrate, and the mixture is heated in an oil bath at 50° C. for 5 h. The solvent is removed in vacuo. The residue is dissolved in saturated aqueous $K_2CO_3$ solution. Continuous extraction of the aqueous layer using a liquid-liquid extraction apparatus (18 h), followed by drying the organic layer over anhydrous $K_2CO_3$ and removal of the solvent in vacuo affords Int 15 as a white solid (91% yield): $^1$H NMR δ 3.8, 3.0–2.8, 2.6–2.5, 2.4–2.3, 1.7, 1.1.

Step O. Preparation of endo-3-azido-1-azabicyclo[2.2.1] heptane (Int 16).

To a mixture of Int 15 (1.0 g, 8.9 mmol) and triphenyl phosphine (3.0 g, 11.5 mmol) in toluene-THF (50 mL, 3:2) in an ice-water bath are added sequentially a solution of hydrazoic acid in toluene (15 mL of ca. 2 M solution) and a solution of diethyl azadicarboxylate (1.8 mL, 11.5 mmol) in toluene (20 mL). The mixture is allowed to warm to rt and stir for 18 h. The mixture is extracted with aqueous 1.0M HCl solution. The aqueous layer is extracted with EtOAc, and the combined organic layers are discarded. The pH of the aqueous layer is adjusted to 9 with 50% aqueous NaOH solution. The aqueous layer is extracted with $CH_2Cl_2$ (3×), and the combined organic layers are washed with brine, dried over $Na_2SO_4$, filtered and concentrated in vacuo. The crude product is purified by flash chromatography on silica gel. Elution with $CHCl_3$—MeOH—$NH_4OH$ (92:7:1) affords Int 16 as a colorless oil (41% yield): $^1$H NMR (CDCl$_3$) δ 4.1, 3.2, 2.8, 2.7–2.5, 2.2, 1.9, 1.5.

Step P. Preparation of endo-3-amino-1-azabicyclo[2.2.1] heptane bis(hydro-para-toluenesulfonate), Amine 2.

A mixture of Int 16 (250 mg, 1.8 mmol) and 10% Pd/C catalyst (12 mg) in EtOH (10 mL) is placed under an atmosphere of hydrogen (15 psi). The mixture is stirred for 1 h at rt. The mixture is filtered through Celite, and the filtrate is concentrated in vacuo. The residue is dissolved in EtOH (10 mL) and para-toluenesulfonic acid monohydrate (690 mg, 3.7 mmol) is added. The mixture is stirred for 30 min, and the precipitate is filtered. The precipitate is washed sequentially with cold EtOH and ether. The precipitate is dried in vacuo to afford Amine 2 as a white solid (85% yield): $^1$H NMR (CD$_3$OD) δ 7.7, 7.3, 4.2, 3.9, 3.6–3.4, 3.3–3.2, 2.4, 2.3, 2.1.

Coupling

EXAMPLE 2(a)

Exo-N-(1-Azabicylo[2.2.1]hept-3-yl)-4-chlorobenzamide Fumarate

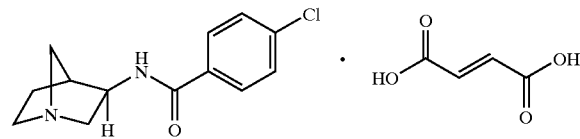

Preparation of exo-N-(1-azabicylo[2.2.1]hept-3-yl)-4-chlorobenzamide.

To a stirred suspension of 4-chlorobenzoic acid (103 mg, 0.66 mmol) in dry $CH_2Cl_2$ (3.0 mL) is added triethylamine (92 μL, 0.66 mmol), followed by diphenylphosphoryl azide (118 μL, 0.55 mmol). In a separate flask, to a stirred solution of Amine 1 (200 mg, 0.44 mmol) in water (0.5 mL) and DMF (3.0 mL) is added triethylamine (245 μL, 1.76 mmol). After 10 min, the amine solution is rapidly added to the benzoic acid solution, and the combined mixture is stirred for 24 h at rt. The reaction mixture is partitioned between saturated aqueous potassium carbonate solution and $CH_2Cl_2$. The aqueous layer is extracted with $CH_2Cl_2$, and the combined organic layers are washed with brine, dried over anhydrous magnesium sulfate, filtered and concentrated in vacuo to a clear residue. The crude product is purified by flash chromatography on silica gel. Elution with chloroform-methanol-ammonium hydroxide (90:9:1) gives 88 mg (80%) of the desired material as a white solid: MS (ESI) m/e: 251 (M+H).

The fumarate salt is then made: To a stirred solution of exo-N-(1-azabicylo[2.2.1]hept-3-yl)-4-chloro-benzamide (81 mg, 0.32 mmol) in acetone (5 mL) is added a hot solution of fumaric acid (37 mg, 0.32 mmol) in isopropyl alcohol (2 mL). The mixture is stirred for 30 min in a 50° C. water bath. The solvents are removed in vacuo and the remaining residue is dissolved in acetone (5 mL). The mixture is stirred overnight at rt. The solid precipitate is collected by filtration and washed with acetone. The solid is dried in vacuo overnight to give 80 mg (67%) of the title compound as a white solid: $^1$H NMR (methanol-d$_4$) δ 7.9, 7.5, 4.2, 3.7, 3.5–3.4, 3.2, 3.0, 2.2, 1.8.

EXAMPLE 2(b)

Endo-N-(1-Azabicylo[2.2.1]hept-3-yl)-4-chloro-benzamide.fumarate:

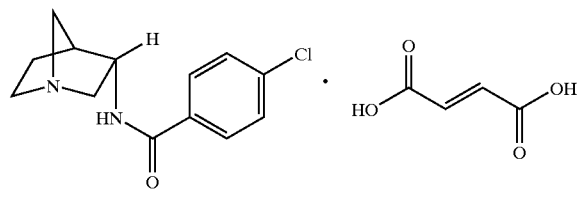

Preparation of Endo-N-(1-azabicylo[2.2.1]hept-3-yl)-4-chloro-benzamide.

To a stirred suspension of 4-chlorobenzoic acid (103 mg, 0.66 mmol) in dry $CH_2Cl_2$ (3.0 mL) is added TEA (92 μL, 0.66 mmol), followed by diphenylphosphoryl azide (118 μL, 0.55 mmol). In a separate flask, to a stirred solution of Amine 2 (200 mg, 0.44 mmol) in water (0.5 mL) and DMF (3.0 mL) is added TEA (245 μL, 1.76 mmol). After 10 min, the amine solution is rapidly added to the benzoic acid solution, and the combined mixture is stirred for 24 h at rt. The reaction mixture is partitioned between saturated aqueous potassium carbonate solution and $CH_2Cl_2$. The aqueous layer is extracted with $CH_2Cl_2$, and the combined organic layers are washed with brine, dried over anhydrous magnesium sulfate, filtered and concentrated in vacuo to a clear residue. The crude product is purified by flash chromatography on silica gel. Elution with $CHCl_3$—MeOH—$NH_4OH$ (90:9:1) gives 55 mg (50%) of the desired material as a white solid. MS (ESI) m/e 251 [M+H].

To a stirred solution of Endo-1-azabicylo[2.2.1]hept-3-yl)-4-chloro-benzamide (55 g, 0.22 mmol) in acetone (5 mL) is added a hot solution of fumaric acid (26 mg, 0.22 mmol) in isopropyl alcohol (2 mL). The mixture is stirred for 30 min in a 50° C. water bath. The solvents are removed in vacuo and the remaining residue is dissolved in acetone (5 mL). The mixture is stirred overnight at rt. The solid precipitate is collected by filtration and washed with acetone. The solid is dried in vacuo overnight to give 49 mg (61%) of Example 2(b) as a white solid. $^1$H NMR (methanol-d$_4$) δ 7.9, 7.5, 6.7, 4.6, 3.8, 3.5–3.2, 3.1, 2.2–2.0.

Using methods described herein, other compounds can be prepared, including any one of or combination of: N-(2-methyl-1-azabicyclo[2.2.1]hept-3-yl)-4-chlorobenzamide, or N-(2-ethyl-1-azabicyclo[2.2.1]hept-3-yl)-4-chlorobenzamide as racemic mixtures or as enantiomers having any of the stereochemistry described herein.

3-Amino-1-azabicyclo[3.2.1]octane ($m^1$ is 1 and $m^2$ is 1):

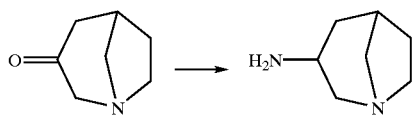

Exo-1-Azabicyclo[3.2.1]octan-3-amine dihydrochloride

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with $CH_2Cl_2$, treated with charcoal, filtered and evaporated. The resulting material is taken up in 1-propanol (45 mL) and heated in a 100° C. oil bath. The solution is treated with sodium metal (6.4 g in portions). Heating continues for 3 h and the mixture is cooled to rt. Water is added carefully and the organic layer is extracted, dried ($MgSO_4$), filtered, acidified with MeOH/HCl(g), and evaporated. 2-Propanol is added and the resulting solid is filtered and dried in vacuo to give exo-1-azabicyclo[3.2.1]octan-3-amine dihydrochloride (exo-[3.2.1]-Amine) in 49% yield. MS for $C_7H_{14}N_2.(HCl)_2$ (ESI) $(M+H)^+$ m/z=127.

Endo-1-Azabicyclo[3.2.1]octan-3-amine dihydrochloride:

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with $CH_2Cl_2$, treated with charcoal, filtered and evaporated. The resulting oxime (3.1 mmol) is treated with acetic acid (30 mL) and hydrogenated at 50 psi over $PtO_2$ (50 mg) for 12 h. The mixture is then filtered and evaporated. The residue is taken up in a minimal amount of water (6 mL) and the pH is adjusted to >12 using solid NaOH. The mixture is then extracted with ethyl acetate (4×25 mL), dried over $MgSO_4$, filtered, treated with ethereal HCl, and evaporated to give the give endo-1-azabicyclo[3.2.1]octan-3-amine dihydrochloride (endo-[3.2.1]-Amine).

Coupling

EXAMPLE 3

Exo-N-[1-azabicyclo[3.2.1]oct-3-yl]-4-chlorobenzamide 4-methylbenzenesulfonate

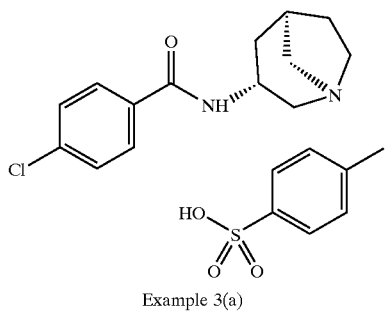

Example 3(a)
3R, 5R-N-(1-azabicyclo[3.2.1]oct-3-yl-
4-chlorobenzamide 4-methylbenzenesulfonate

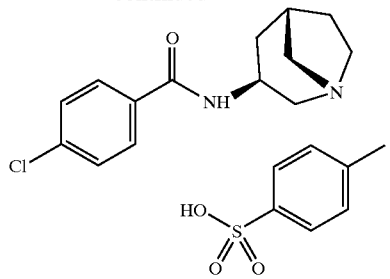

Example 3(b)
3S, 5S-N-(1-azabicyclo[3.2.1]oct-3-yl-
4-chlorobenzamide 4-methylbenzenesulfonate A mixture of exo-[3.2.1]-Amine (0.335 g, 2.14 mmol), 4-chlorobenzoic acid (0.426 g, 2.14 mmol), THF (35 mL), DIEA (1.2 mL, 6.89 mmol), and DMF (10 mL) is cooled in an ice bath and treated with HATU (0.874 g, 2.30 mmol). The mixture is warmed to rt overnight and is evaporated. The residue is diluted with $CHCl_3$ and washed with aqueous NaOH (1N). The organic layer is dried ($MgSO_4$), filtered, evaporated, and the resulting oil purified by flash column chromatography (1:9:90; conc. $NH_4OH$—MeOH—$CHCl_3$). The p-toluenesulfonate salt is formed and triturated with EtOAc/hexane to yield the desired product (0.589 g, 63%). MS for $C_{14}H_{17}ClN_2O.C_8H_8O_3S$ (ESI) $(MH)^{+m/z}$=265.

The enantiomers of the compound as the p-toluenesulfonate salt are separated using a 5×50 cm Chiralcel OD column at 30° C. using a 25% isopropanol/75% heptane/0.1% diethylamine (v/v/v) mobile phase, 84 mL/min. flow rate, and UV detection at 225 nm. Injections of 250 mg (25 mL of 3:1 IPA/$CHCl_3$) are made. Two collections are made with one being from 8–14 min and the second one being from 20–30 min. Reanalysis on a 0.46×25 cm Chiralcel OD-H column, 15% IPA/85% heptane/0.1% DEA mobile phase, 0.5 mL/min. flow rate, UV detection at 225 nm. is used. The compound having the 3R,5R stereochemistry eluted at 11.7 min while the compound having the 3S,5S stereochemistry eluted at 23.5 min.

Example 3(a): The compound is partitioned between 1N NaOH and $CH_2Cl_2$, washed with $H_2O$ and dried ($MgSO_4$). The p-toluenesulfonate salt is formed using p-TsOH monohydrate and EtOH, triturated with IPA, and dried in vacuo to yield (3R,5R)-N-(1-azabicyclo[3.2.1]oct-3-yl)-4-chlorobenzamide 4-methylbenzenesulfonate (0.171 g, 18%). MS (ESI) for $C_{14}H_{17}ClN_2O.C_8H_8O_3S$ (MH)+m/z=265.

Example 3(b): The compound is partitioned between 1N NaOH and $CH_2Cl_2$, washed with $H_2O$ and dried ($MgSO_4$). The p-toluenesulfonate salt is formed using p-TsOH monohydrate and EtOH, triturated with IPA, and dried in vacuo to yield (3S,5S)-N-(1-azabicyclo[3.2.1]oct-3-yl)-4-chlorobenzamide 4-methylbenzenesulfonate (0.170 g, 18%). MS (ESI) for $C_{14}H_{17}ClN_2O.C_8H_8O_3S$ (MH)+m/z=265.

Using methods described herein, other compounds can be prepared, including any one of or combination of:

N-[2-methyl-1-azabicyclo[3.2.1]oct-3-yl]-4-chlorobenzamide,

N-[4-methyl-1-azabicyclo[3.2.1]oct-3-yl]-4-chlorobenzamide,

N-[2-ethyl-1-azabicyclo[3.2.1]oct-3-yl]-4-chlorobenzamide, or

N-[4-ethyl-1-azabicyclo[3.2.1]oct-3-yl]-4-chlorobenzamide, as racemic mixtures or as enantiomers having any of the stereochemistry described herein.

3-Amino-1-azabicyclo[3.2.2]nonane ($m^1$ is 1 and $m^2$ is 2):

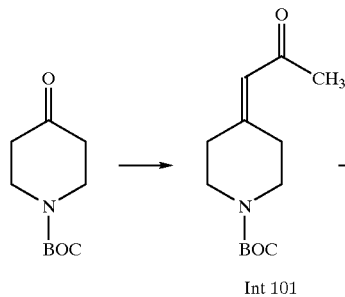
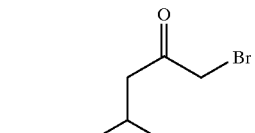
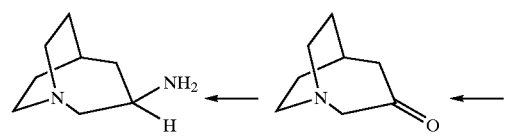
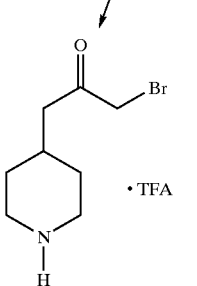

Preparation of tert-butyl 4-(2-oxopropylidene)piperidine-1-carboxylate (Int 101):

Sodium hydride (60% oil dispersion, 2.01 g, 50.2 mmol) is washed with pentane (3×) and suspended in dry THF (40 mL). The solution is cooled to 0° C. before diethyl (2-oxopropyl)phosphonate (9.75 g, 50.2 mmol) is added dropwise. After complete addition, the solution is warmed to rt and stirred for 30 min. tert-Butyl 4-oxo-1-piperidinecarboxylate (5.0 g, 25.1 mmol) is added in portions over 10 min, followed by stirring at rt for 2 h. A saturated aqueous solution of ammonium chloride is added, followed by dilution with ether. The organic layer is extracted with water. The organic layer is dried over anhydrous MgSO$_4$, filtered and concentrated to a yellow oil. The crude product is purified by flash chromatography on silica gel. Elution with hexanes-ether (60:40) gives 4.5 g (75%) of Int 101 as a white solid: $^1$H NMR (CDCl$_3$) δ 6.2, 3.5, 3.4, 2.9, 2.3, 2.2, 1.5.

Preparation of tert-butyl 4-(2-oxopropyl)piperidine-1-carboxylate (Int 102):

A mixture of Int 101 (4.5 g, 19 mmol) and 10% palladium on activated carbon (450 mg) in EtOH (150 mL) is placed in a Parr bottle and hydrogenated for 5 h at 50 psi. The mixture is filtered through Celite, and the filtrate is concentrated in vacuo to afford 4.3 g (94%) of Int 102 as a clear oil: $^1$H NMR (CDCl$_3$) δ 4.1, 2.8, 2.4, 2.2, 2.0, 1.7, 1.5, 1.1.

Preparation of tert-butyl 4-(3-bromo-2-oxopropyl)piperidine-1-carboxylate (Int 103):

To a stirred solution lithium hexamethyldisilylamide in THF (20. 0 mL, 1.0 M) in a −78° C. bath is added chlorotrimethylsilane (11.0 mL, 86.4 mmol) dropwise. The mixture is stirred at −78° C. for 20 min, followed by addition of Int 102 (3.21 g, 13.3 mmol) in a solution of THF (50 mL) dropwise. After complete addition, the mixture is stirred at −78° C. for 30 min. The mixture is warmed to 0° C. in an ice-water bath and phenyltrimethylammonium tribromide (5.25 g, 14.0 mmol) is added. The mixture is stirred in an ice-bath for 30 min, followed by the addition of water and ether. The aqueous layer is washed with ether, and the combined organic layers are washed with saturated aqueous sodium thiosulfate solution. The organic layer is dried over anhydrous MgSO$_4$, filtered and concentrated in vacuo to afford a yellow oil. The crude product is purified by flash chromatography on silica gel. Elution with hexanes-ether (60:40) gives 2.2 g (52%) of Int 103 as a lt. yellow oil: $^1$H NMR (CDCl$_3$) δ 4.2–4.1, 3.9, 2.8, 2.7, 2.6, 2.1–2.0, 1.7, 1.5, 1.2–1.1.2.

Preparation of 1-bromo-3-piperidin-4-ylacetone trifluoroacetate (Int 104):

To a stirred solution of Int 103 (2.2 g, 6.9 mmol) in CH$_2$Cl$_2$ (30 mL) in an ice-water bath is added trifluoroacetic acid (10 mL, 130 mmol). The mixture is stirred at 0° C. for 30 min. The volatiles are removed in vacuo to afford 2.0 g (87%) of Int 104 as a yellow residue: MS (ESI) for C$_8$H$_{15}$BrNO [M+H] m/e 220.

Preparation of 1-azabicyclo[3.2.2]nonan-3-one (Int 105):

To a stirred solution of DIEA (13 mL) in acetonitrile (680 mL) at reflux temperature is added a solution of Int 104 (2.0 g, 6.0 mmol) in acetonitrile (125 mL) over a 4 h period via syringe pump. The mixture is kept at reflux temperature overnight. The mixture is concentrated in vacuo and the remaining residue is partitioned between a saturated aqueous potassium carbonate solution and CHCl$_3$—MeOH (90:10). The aqueous layer is extracted with CHCl$_3$—MeOH (90:10), and the combined organic layers are dried over MgSO$_4$, filtered and concentrated in vacuo to a brown oil. The crude product is purified by flash chromatography on silica gel. Elution with CHCl$_3$—MeOH—NH4OH (95:4.5:0.5) gave 600 mg (72%) of Int 105 as a clear solid: $^1$H NMR (CDCl$_3$) δ 3.7, 3.3–3.2, 3.1–3.0, 2.7, 2.3, 2.0–1.8.

Preparation of 1-azabicyclo[3.2.2]nonan-3-amine bis(4-methylbenzenesulfonate) ([3.2.2]-Amine):

To a stirred mixture of Int 105 (330 mg, 2.4 mmol) and sodium acetate.trihydrate (670 mg, 4.8 mmol) in EtOH (6.0 mL) is added hydroxylamine.hydrochloride (200 mg, 2.8 mmol). The mixture is stirred at rt for 10 h. The mixture is filtered and the filtrate is concentrated in vacuo to a yellow solid. To a solution of the solid (350 mg, 2.3 mmol) in n-propanol (30 mL) at reflux temperature is added sodium metal (2.0 g, 87 mmol) in small portions over 30 min. Heating at reflux is continued for 2 h. The solution is cooled to rt and brine is added. The mixture is extracted with n-propanol, and the combined organic layers are concentrated in vacuo. The residue is taken up in $CHCl_3$ and the remaining solids are filtered. The filtrate is dried over anhydrous $MgSO_4$, filtered and concentrated in vacuo to a clear solid. To a stirred solution of the solid (320 mg, 2.3 mmol) in EtOH (4 mL) is added p-toluenesulfonic acid monohydrate (875 mg, 4.6 mmol). The solution is warmed in a water bath to 45° C. for 30 min, followed by concentration of the solvent to afford 710 mg (62%) of [3.2.2]-Amine as a white solid: $^1H$ NMR ($CD_3OD$) δ 7.7, 7.3, 4.1–3.9, 3.6–3.4, 2.6–2.5, 2.4, 2.2–2.1, 2.1–2.0, 1.9.

Resolution of Stereoisomers:

The amine can be coupled to form the appropriate amide as a racemic mixture. The racemic mixture can then be resolved by chromatography using chiral columns or chiral HPLC, techniques widely known in the art, to provide the requisite resolved enantiomers 3(R) and 3(S) of said amide.

Using methods described herein, other compounds can be prepared, including any one of or combination of:

N-(1-azabicyclo[3.2.2]non-3-yl)-4-chlorobenzamide,

N-(4-methyl-1-azabicyclo[3.2.2]non-3-yl)-4-chlorobenzamide,

N-(2-methyl-1-azabicyclo[3.2.2]non-3-yl)-4-chlorobenzamide,

N-(4-ethyl-1-azabicyclo[3.2.2]non-3-yl)-4-chlorobenzamide, or

N-(2-ethyl-1-azabicyclo[3.2.2]non-3-yl)-4-chlorobenzamide, as racemic mixtures or as enantiomers having the stereochemistry as described herein.

Materials and Methods for Identifying Binding Constants:

Membrane Preparation. Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000× g for 10 minutes at 4° C. The supernatant is collected and centrifuged at 20,000× g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at room temperature and diluted with Kreb's—20 mM Hepes buffer pH 7.0 (at room temperature) containing 4.16 mM $NaHCO_3$, 0.44 mM $KH_2PO_4$, 127 MM NaCl, 5.36 mM KCl, 1.26 mM $CaCl_2$, and 0.98 mM $MgCl_2$, so that 25–150 μg protein are added per test tube. Protein concentration is determined by the Bradford method (Bradford, M. M., *Anal. Biochem.*, 72, 248–254, 1976) using bovine serum albumin as the standard.

Binding Assay. For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 1 μM MLA, added before the radioligand. In competition studies, drugs are added in increasing concentrations to the test tubes before addition of approximately 3.0 to 4.0 nM [$^3H$]-MLA. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis. In competition binding studies, the inhibition constant (Ki) was calculated from the concentration dependent inhibition of [$^3H$]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

| Example | Ki (nM) |
|---|---|
| Example 1(a) | 26 |
| Example 1(b)(i) | 65–140 |
| Example 3 (racemic) | 115 |
| Example 3 (3R, 5R) | 18 |
| Example 3 (3S, 5S) | >1000 |

What is claimed:

1. A compound of the Formula I:

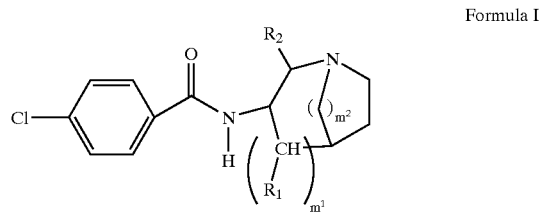

Formula I wherein $m^1$ is 0 or 1;

$m^2$ is 1 or 2, provided that when $m^1$ is 0, $m^2$ is 1;

$R^1$ is —H, alkyl, halogenated alkyl, substituted alkyl, cycloalkyl, or phenyl;

$R^2$ is —H, alkyl, halogenated alkyl, substituted alkyl, cycloalkyl, or phenyl;

or a pharmaceutically acceptable salt, pure enantiomer, or racemic mixture thereof.

2. The compound of claim 1, wherein $m^1$ is 0 and $m^2$ is 1.

3. The compound of claim 2, wherein the compound is N-(1-azabicylo[2.2.1]hept-3-yl)-4-chloro-benzamide, N-(2-methyl-1-azabicyclo[2.2.1]hept-3-yl)-4-chlorobenzamide, N-(2-ethyl-1-azabicyclo[2.2.1]hept-3-yl)-4-chlorobenzamide or a pharmaceutically acceptable salt, pure enantiomer, or racemic mixture thereof.

4. The compound of claim 1, wherein $m^1$ is 1 and $m^2$ is 1.

5. The compound of claim 4, wherein the compound is N-[1-azabicyclo[3.2.1]oct-3-yl]-4-chlorobenzamide, N-[2-methyl-1-azabicyclo[3.2.1]oct-3-yl]-4-chlorobenzamide, N-[4-methyl-1-azabicyclo[3.2.1]oct-3-yl]-4-chlorobenzamide, N-[2-ethyl-1-azabicyclo[3.2.1]oct-3-yl]-4-chlorobenzamide, N-[4-ethyl-1-azabicyclo[3.2.1]oct-3-yl]-4-chlorobenzamide or a pharmaceutically acceptable salt, pure enantiomer, or racemic mixture thereof.

6. The compound of claim 1, wherein $m^1$ is 1 and $m^2$ is 2.

7. The compound of claim 6, wherein the compound is N-(1-azabicyclo[3.2.2]non-3-yl)-4-chlorobenzamide, N-(4-methyl-1azabicyclo[3.2.2]non-3-yl)-4-chlorobenzamide, N-(2-methyl-1-azabicyclo[3.2.2]non-3-yl)-4-chlorobenzamide, N-(4-ethyl-1-azabicyclo[3.2.2]non-3-yl)-4-chlorobenzamide, N-(2-ethyl-1-azabicyclo[3.2.2]non-3-yl)-4-chlorobenzamide or a pharmaceutically acceptable salt, pure enantiomer, or racemic mixture thereof.

8. A method for treating schizophrenia in a mammal in need thereof comprising administering to the mammal a therapeutically effective amount of compound of claim 1.

9. The method of claim 8, wherein the compound is:

N-(1-azabicylo[2.2.1]hept-3-yl)-4-chloro-benzamide,

N-(2-methyl-1-azabicyclo[2.2.1]hept-3-yl)-4-chlorobenzamide,

N-(2-ethyl-1-azabicyclo[2.2.1]hept-3-yl)-4-chlorobenzamide or a pharmaceutically acceptable salt, pure enantiomer, or racemic mixture thereof.

10. The method of claim 8, wherein the compound is:

N-[1-azabicyclo[3.2.1]oct-3-yl]-4-chlorobenzamide,

N-[2-methyl-1-azabicyclo[3.2.1]oct-3-yl]-4-chlorobenzamide,

N-[4-methyl-1-azabicyclo[3.2.1]oct-3-yl]-4-chlorobenzamide,

N-[2-ethyl-1-azabicyclo[3.2.1]oct-3-yl]-4-chlorobenzamide,

N-[4-ethyl-1-azabicyclo[3.2.1]oct-3-yl]-4-chlorobenzamide or a pharmaceutically acceptable salt, pure enantiomer, or racemic mixture thereof.

11. The method of claim 8, wherein the compound is:

N-(1-azabicyclo[3.2.2]non-3-yl)-4-chlorobenzamide,

N-(4-methyl-1-azabicyclo[3.2.2]non-3-yl)-4-chlorobenzamide,

N-(2-methyl-1-azabicyclo[3.2.2]non-3-yl)-4-chlorobenzamide,

N-(4-ethyl-1-azabicyclo[3.2.2]non-3-yl)-4-chlorobenzamide,

N-(2-ethyl-1-azabicyclo[3.2.2]non-3-yl)-4-chlorobenzamide or a pharmaceutically acceptable salt, pure enantiomer, or racemic mixture thereof.

12. The method of claim 8, wherein the compound is administered rectally, topically, orally, sublingually, or parenterally.

13. The method of claim 8, wherein said compound is administered from about 0.001 to about 100 mg/kg of body weight of said mammal per day.

14. The method of claim 8, wherein said compound is administered from about 0.1 to about 50 mg/kg of body weight of said mammal per day.

* * * * *